United States Patent [19]

Stahr

[11] 3,964,981

[45] June 22, 1976

[54] METHOD FOR POLAROGRAPHIC ANALYSIS USING AN ELECTRODE OF TANTALUM/CARBON MATERIAL

[75] Inventor: Henry M. Stahr, Ogden, Iowa

[73] Assignee: Iowa State University Research Foundation, Inc., Ames, Iowa

[22] Filed: Sept. 20, 1973

[21] Appl. No.: 399,075

Related U.S. Application Data

[63] Continuation of Ser. No. 244,133, April 14, 1972, abandoned.

[52] U.S. Cl. .............................. 204/1 T; 148/20.3; 204/195 R; 204/290 F; 204/294
[51] Int. Cl.² .................. G01N 27/48; G01N 27/30
[58] Field of Search ............ 204/1 T, 195 R, 290 F, 204/294; 148/20.3

[56] References Cited
UNITED STATES PATENTS

| | | |
|---|---|---|
| 3,028,324 | 4/1962 | Ransley.......................... 204/294 X |
| 3,266,948 | 8/1966 | McGuire........................... 148/20.3 |
| 3,324,025 | 6/1967 | Hackerman et al. ......... 204/290 F X |
| 3,523,044 | 8/1970 | Johansen ...................... 148/20.3 X |

*Primary Examiner*—G. L. Kaplan
*Attorney, Agent, or Firm*—Dawson, Tilton, Fallon & Lungmus

[57] ABSTRACT

An electrode for an electrochemical cell, such as may be used in polarographic measurements, is formed by vapor deposition of carbon on a tantalum substrate. It can be formed to a desired shape while retaining all the properties of the metal, and it has a large surface and is thus very sensitive. The electrode is inert, will not oxidize over a wide useful range of applied voltages, and exhibits no hysteresis effect when the polarity is reversed.

1 Claim, 3 Drawing Figures

METHOD FOR POLAROGRAPHIC ANALYSIS USING AN ELECTRODE OF TANTALUM/CARBON MATERIAL

RELATED APPLICATIONS

This is a continuation application of copending application Ser. No. 244,133, filed Apr. 14, 1972 and now abandoned.

BACKGROUND AND SUMMARY

The present invention relates to electrochemical cells; and more particularly, it pertains to an improved electrode for use in an electrochemical cell in the field of voltammetry.

Broadly speaking, electrochemical cells include a reference electrode and an indicator or active electrode immersed in an electrolyte, together with some means for measuring the voltage between the electrodes and the current flowing through the electrodes. If a separate, external source of current or voltage is provided to energize the electrodes, the cell is sometimes referred to as a forced cell.

A passive cell is one in which no external source of voltage or current is applied to the electrodes. An example of this type of cell is an ion-selective electrode and reference electrode used to measure hydrogen in activity.

Polarographic measuring systems apply a potential to a forced cell which operates on the principle that when a varying electromotive force is applied to the electrodes of the cell, the resulting current is representative of the concentration of a trace material (being reduced) in the electrolyte. One electrode is energized with a positive polarity and it is resistant to changes. The non-polarizable electrode exhibits a current which is representative of the reduction process taking place. There is an exponentially increasing current at a particular voltage which is characteristic of (and hence identifies) the particular material being investigated.

In polarography, probably the most commonly used type of electrode is called a dropping mercury electrode. It includes a length of capillary tubing, such as a marine barometer through which pure metallic mercury flows. As mercury flows through the tube, drops form at the tip of the capillary. As each drop grows to a certain size, it falls off and another drop begins to form. The dropping mercury electrode as well as a reference are placed into the solution under study. Other systems use two working electrodes. The cell voltage is then applied to them, and a reference electrode which is not biased is used to directly measure the cell voltage.

Typically, the capillary tubing will be fed by a larger source of mercury into which a metallic electrical contact, such as a platinum wire, may be provided to complete the circuit.

As each drop forms, the area increases continuously, thus increasing the current flow until the drop falls, at which time the current decreases to zero, and the cycle repeats itself. The currents involved are normally so small (of the order of microamps) and the voltage so nominal (of the order of one-two volts) that the iR drop across the electrolyte may be ignored when compared with the voltage at the working electrode. The current oscillates between a maximum and a minimum value so as to trace out the particular voltage-current characteristic for the material under study.

As already mentioned, a typical voltage-current characteristic for the oxidation or reduction of a substance starts out linearly and then increases exponentially at a particular applied potential characteristic of the substance. The curve then levels off to form a plateau. Reduction occurs only in the narrow layer surrounding the electrode, and the leveling off is caused by the ability of the species to diffuse through this layer and to come into contact with the electrode surface. Hence, the plateau is sometimes referred to as the diffusion plateau, after Hevorsky, the inventor of polarography, as described by Meites, et al in *Advanced Analytical Chemistry*, McGraw-Hill (1958).

This type of polarographic cell employs platinum or gold as the indicator electrodes, and this type of electrode may be agitated to limit the sensed current to diffusion of the reducible substance to the electrode, thereby increasing the diffusion current in relation to the polarizing current. The diffusion current also depends on the size of the electrode, the temperature of the solution, the concentration of diffusing material, the electrode material, properties of the solution/electrode film, etc.

Another system used a disc and rotating ring for electrodes, see Johnson, et al, *Analytical Chemistry*, Vol. 40, No. 3 (1968). Other methods of voltammetry are described in Nicholson, et al, *Analytical Chemistry*, Vol. 37, No. 2 (1965).

In practice, the equilibrium of the electronic exchange electrode-solution is not achieved instantaneously, requiring that the potential applied to the electrodes be raised to a higher value than that theoretically expected. This difference or "lag" with respect to the reversible value is referred to as "overvoltage". Overvoltage increases with current, and it results in a hysteresis effect relative to the reversible value of voltage. For example, it is known that the overvoltage of $H^+$ on mercury is about 600 mv. whereas discharge of $H_2$ occurs as expected when polished platinum is used as the indicator electrode. A dropping mercury electrode has certain inherent limitations, one of which is that metallic mercury is oxidized fairly readily. Thus, even in solutions containing only non-complexing anions, such as perchlorate and nitrate, the oxidation of mercury begins at a potential near +0.4 volts. In such a system, the concentration of dissolved mercurous or mercuric ions present around the drop will be quite large even at potentials onyl very slightly more positive than +0.4 volts. This gives rise to a large negative current, rendering it impossible to measure or even detect a small additional current due to the reduction or oxidation of the substance under study. This limit of the range of potentials within which useful data can be obtained is even more restrictive in solutions containing ions like chloride, cyanide and hydroxide, which combine with either mercurous or mercuric ion and thus facilitate the oxidation of metallic mercury. Another disadvantage in the use of mercury as an electrode is that it readily alloys with heavy metals so that the process may not be reversible under conditions of long polarization.

The present invention provides for an electrode in an electrochemical cell, such as are used in polarography, which is formed from tantalum and carbon. Tantalum is formed into the desired shape of the electrode, and it is then placed in a vacuum furnace in the presence of carbon and heated to 800°–1000°C. until the surface of the tantalum metal assumes a gold color. The resulting composition is the electrode material which I have found to have, surprisingly, an extreme lack of reactivity. For example, whereas tantalum is dissolved by hydroflouric acid, this material is not affected by it. Further, whereas carbon is visibly attacked by aqua regia, this material is not attacked by aqua regia. In addition, this material is highly resistant to electrochemical corrosion. These characteristics are advantageous to any electrode in an electrochemical cell, and it is therefore believed that the material of the present invention has application as an electrode in electrochemical cells broader than that polarography, although most of the results discussed hereinafter are based upon polarographic studies.

The material of the present invention has advantages over platinum as used as an electrode in that it is much more economical than platinum and it is not oxidized or dissolved in HF or aqua regia. When a positive potential is applied to platinum, it becomes oxidized, and if the electrode is then scanned negatively, a hysteresis effect of the type already mentioned is exhibited. Platinum also forms alloys with heavy metals. The material of the present invention has advantages over mercury as an electrode material because it does not alloy with the heavy metals. This is a particularly important characteristic in toxicological studies, particularly under prevailing circumstances wherein the heavy metals are among the most prominent poisons found in tissue.

The present invention also permits forming electrodes of various shapes by forming the tantalum substrate first (while in its metallic form) and then coating with carbon. When scanned in a polarographic cell, an electrode of the tantalum/carbon material exhibits no evidence of hysteresis, thereby resulting in a sharper, more highly sloped voltage-current characteristic for a particular substance being studied. It appears that this particular property also indicates that there is no oxidation of the material or any other film formation on the surface of the material since it is believed that oxidation is a principal cause of the overvoltage and hysteresis phenomena mentioned above for platinum and other metals. Because of the physical form of the tantalum prior to firing in the vacuum furnace, the resulting electrode can be made to have very high surface area, and this permits the detection of substances at levels much lower than had been possible with conventional dropping mercury electrodes or with platinum electrodes.

The advantageous properties of the present invention would also be useful in electrolytic cells, for example, in production-size commercial cells for the production of chlorine by electrolysis or in other such cells. Normally, the range of voltages employed will be limited by the nature of the electrolyte rather than any voltage limitation on the carbon/tantalum material.

Other features and advantages of the present invention will be apparent to persons skilled in the art from the following detailed description of preferred embodiments accompanied by the attached drawing.

THE DRAWING

DETAILED DESCRIPTION

Figure 1:
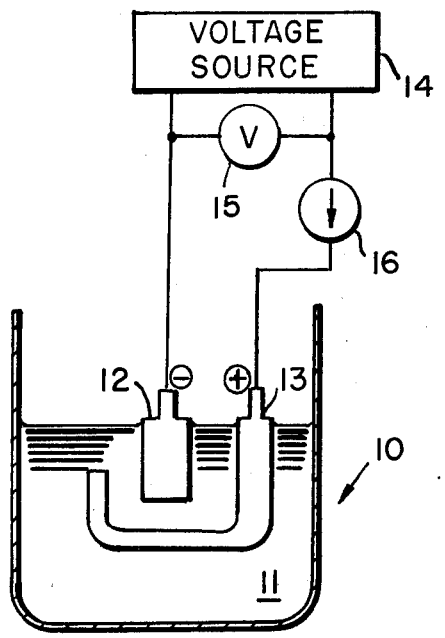
FIG. 1 is a schematic diagram illustrating a system incorporating the present invention.

Referring first to FIG. 1, there is shown a polarographic cell generally designated by reference numeral 10 including an electrolyte solution 11 under study, an active electrode designated 12 and formed of the tantalum/carbon material to be described presently, and a reference electrode 13 which may be any standard reference electrode such as are conventionally used, such as silver/silver-chloride or calomel. Alternatively, the reference electrode 13 may be of the same tantalum/carbon material as the active electrode 11. A source of voltage 14 energizes the electrodes 12, 13 in the polarity indicated, and a voltage measuring means 15, such as a voltmeter or electrometer, measures the voltage across the electrodes 12, 13. An ammeter 16 measures the current flowing between the electrodes 12, 13.

Figure 2:
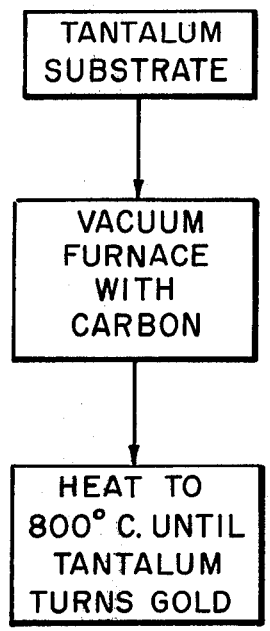
FIG. 2 is a process flow chart illustrating the making of an electrode out of the tantalum/carbon material.

Turning now to FIG. 2, there is shown a process diagram illustrating the making of the active electrode 12, and it includes the steps of providing a tantalum base, such as a thin sheet of tantalum of the order of one mil. thick, and then placing it in a vacuum furnace with carbon blocks on either side of the sheet of tantalum. The vacuum furnace is then evacuated to a pressure of $10^{-6}$ millimeters of mercury and heated to approximately 800°C. until the tantalum turns a gold color, and this signifies the proper formation of the tantalum/carbon material forming the electrode 12. Alternatively, the electrode may be suspended over a carbon crucible and heated in a vacuum lower than $10^{-7}$ mm. Hg to 1000°–1200°C. The carbon vaporizes and condenses on the tantalum substrate to form a very thin film. The film is so thin that the nature of the material thus formed does not readily lend itself to analysis. For this reason, and because the physical chemistry involved is so complex, the manner of making the carbon/tantalum material is the only manner I have to define it, together with the characteristic of almost total lack of reactivity.

The material is not tantalum carbide, although tantalum carbide may be present in small amounts. Rather, it appears that a complex interaction takes place on the surface of the tantalum when it combines with the vaporized carbon. The temperature of the furnace must be held below the temperature at which tantalum and carbon alloy, although time also is of importance since it requires some time for carbon to diffuse into the tantalum to form the alloy. This is why I chose to observe the turning to gold color in a vacuum as indicative that the desired compound has been formed. The alloy, of course, possesses none of the desired properties, and it can be observed in formation by turning a characteristic gray color, from the gold, indicating the formation has been allowed to continue too long.

The property of the electrode thus formed which is most noteworthy and surprising in view of the susceptibility of carbon to attack by aqua regia and tantalum and other alloys to attack by HF, is the lack of reactivity or almost complete inertness of the electrode. It does not dissolve in hydroflouric acid, nor does it exhibit any evidence of corrosion when polarized 1.5 volts in aqueous solution, either positively or negatively. Further, the electrode material does not form alloys with heavy metals investigated, and it can be shaped using conventional powder metallurgical techniques, if it is desired to increase the sensitivity of the system because through these techniques, an electrode may be formed having a very large surface area for a given cross sectional area.

Figure 3:
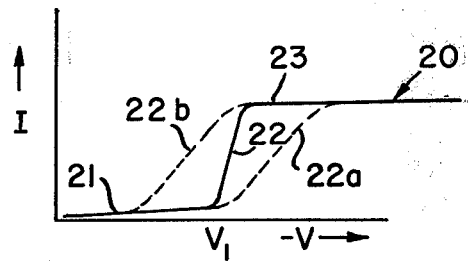
FIG. 3 is a current-voltage characteristic of the type exhibited in polarography.

Referring now to FIG. 3, there is shown in solid an idealized current-voltage characteristic of a reducible material, the characteristic being generally designated by reference numeral 20. It will be observed that as the voltage increases in a negative direction, the slope of the characteristic at 21 is relatively flat and not steep. When the voltage approaches the potential V, the increase in current is exponential as at 22 until a diffusion plateau 23 is reached, after which the current again levels out. The current at the voltage $V_1$, of course, is indicative of the presence of a particular substance, and the magnitude of the diffusion plateau 23 is representative of the amount of the substance present. That is, $V_1$ is characteristic of the species where one-half the activity is both oxidized and reduced and thus it is the thermodynamic potential for the material in solution being reduced.

If the electrode developed a film during reduction, the shape of the characterizing portion 22 may turn out like the dashed line 22a, for example. It will be noticed that not only is there an offset or lag in the response, but the slope is much less than for the solid portion 22, and therefore not as distinguishing. Further, when the polarity is reversed, the return path for an oxidized electrode will follow the dashed line 22b; and the total characteristic 22, 22a, 21, 22b can be seen to exhibit the hysteresis effect which is not present in the inventive system as long as the applied voltage is between ± 1.5 v.

An electrode was made of the tantalum/carbon material as disclosed above and studies were made by incorporating the inventive electrode into a Model 14 Polarograph manufactured by E. H. Sargent and Co., now Sargent-Welch of Chicago, Illinois.

I have demonstrated that the tantalum/carbon material described can be used in a forced cell for the electrochemical reduction or oxidation of an electroactive species in solution, including metals and oxygen. Further, the electrode can be used as a collecting electrode polarized to collect the electroactive species of interest. In this case, the amount of substance removed may be monitored either by measuring (integrating) the plating current as the electroactive material deposits on the electrode or by stripping the material from the electrode by anodically scanning the electrode (i.e., reversing polarity) which has collected the material through cathodization.

The substance has also been found to have the property that it does not alloy with heavy metals, the heavy metals will simply plate out on the surface of the material and the process may be reversed, or the metals may be recovered completely, if desired.

The electrode has particular application in biomedical applications because it permits a greater accuracy and reliability of measurements due to the fact that there is no film formed on the exterior of the material, and it is thought that its highly non-reactive characteristic would be more favorable when used in connection with work on animals.

The material is much less expensive than platinum, and it has the further advantage over platinum in that no film forms on its surface, and it can be shaped, as indicated.

As a non-corrosive electrode, the tantalum/carbon material of the present invention, by replacing mercury, would help to reduce the scattering of mercury and amalgams in the environment.

Having thus disclosed in detail a preferred embodiment of the invention, persons skilled in the art will be able to modify certain of the steps and devices which have been disclosed and to substitute equivalent elements for those described while continuing to practice the principle of the invention; and it is, therefore, intended that all such modifications and substitutions be covered as they are embraced within the spirit and scope of the appended claims.

I claim:

1. In a method of polarographic analysis of a species in an electrolyte including the steps of contacting said electrolyte with a reference electrode; contacting said electrolyte with an active electrode; applying an increasing voltage between said electrodes; and measuring the current flowing between said electrodes to produce an abruptly increasing current followed by a generally constant current, the voltage at which said increasing current appears being representative of a particular species and the magnitude of said constant current being representative of the quantity of the identified species; the improvement wherein said step of contacting said electrolyte with an active electrode comprises contacting said electrolyte with a tantalum/carbon material formed by vacuum-depositing carbon on a tantalum substrate by heating tantalum in a vacuum furnace in the presence of carbon at a temperature in the range 800° – 1,200°C. and depositing carbon on said tantalum substrate until the surface of said substrate turns gold, said material characterized in being inert to hydrofluoric acid and aqua regia.

* * * * *